(12) United States Patent
Baker et al.

(10) Patent No.: US 11,213,507 B2
(45) Date of Patent: Jan. 4, 2022

(54) MRSA BIOFILM INHIBITION

(71) Applicants: University of South Florida, Tampa, FL (US); UAB Research Foundation, Birmingham, AL (US)

(72) Inventors: Bill J. Baker, Tampa, FL (US); Lindsey N. Shaw, Tampa, FL (US); James Bruce McClintock, Birmingham, AL (US); Charles D. Amsler, Pelham, AL (US); Jacqueline Lee Fries, Sarasota, FL (US); Witowski G. Christopher, Sarasota, FL (US); Renee M. Fleeman, Tampa, FL (US)

(73) Assignees: UNIVERSITY OF SOUTH FLORIDA, Tampa, FL (US); UAB RESEARCH FOUNDATION, Birmingham, AL (US)

( * ) Notice: Subject to any disclaimer, the term of this patent is extended or adjusted under 35 U.S.C. 154(b) by 679 days.

(21) Appl. No.: 16/081,494

(22) PCT Filed: Apr. 17, 2017

(86) PCT No.: PCT/US2017/026608
§ 371 (c)(1),
(2) Date: Aug. 31, 2018

(87) PCT Pub. No.: WO2017/177142
PCT Pub. Date: Oct. 12, 2017

(65) Prior Publication Data
US 2021/0205266 A1    Jul. 8, 2021

Related U.S. Application Data

(60) Provisional application No. 62/319,661, filed on Apr. 7, 2016.

(51) Int. Cl.
*A61K 31/365* (2006.01)
*A61P 31/04* (2006.01)
*A61K 9/00* (2006.01)

(52) U.S. Cl.
CPC .......... *A61K 31/365* (2013.01); *A61K 9/0014* (2013.01); *A61P 31/04* (2018.01); *C07B 2200/13* (2013.01)

(58) Field of Classification Search
CPC ..... A61K 31/365; A61K 9/0014; A61P 31/04; C07B 2200/13
(Continued)

(56) References Cited

U.S. PATENT DOCUMENTS

2003/0065025 A1   4/2003  Crews et al.
2016/0030388 A1   2/2016  Baker et al.

FOREIGN PATENT DOCUMENTS

WO   2014/161902 A1   10/2014

OTHER PUBLICATIONS

Akers et al., "Biofilms and persistent wound infections in United States military trauma patients: a case-control analysis," BMC Infect. Dis., 2014, 14, 190.
(Continued)

*Primary Examiner* — Taylor V Oh

(57) ABSTRACT

Provided is a darwinolide compound having a previously undescribed carbon skeleton and the crystalline form thereof. Also provided are processes of isolating darwinolide, compositions comprising darwinolide, and methods of treating infection, such as a methicillin-resistant *Staphylococcus aureus* biofilm infection.

18 Claims, 12 Drawing Sheets

(58) Field of Classification Search
USPC .......................................................... 514/468
See application file for complete search history.

(56) References Cited

OTHER PUBLICATIONS

Bobzin et al., "Diterpenes from the Marine Sponge *Aplysilla polyrhaphis* and the Dorid Nudibranch *Chromodoris norrisi*," J. Org. Chem., 1989, 54, 3902-3907.
Dolomanov et al., "OLEX2: A Complete Structure Solution, Refinement and Analysis Program," J. Appl. Cryst., 2009, 42, 339-341.
Fleeman et al., "Combinatorial Libraries As a Tool for the Discovery of Novel, Broad-Spectrum Antibacterial Agents Targeting the ESKAPE Pathogens," J. Med. Chem., 2015, 58, 3340-3355.
Hooft et al., "Determination of absolute structure using Bayesian statistics on Bijvoet differences," J. Appl. Cryst., 2008, 41, 96-103.
International Search Report and Written Opinion for Application No. PCT/US2017/026608 dated Sep. 8, 2017 (13 pages).
Karuso et al., "Terpenoid Constituents of Morphologically Similar Sponges in the Family Aplysillidae," Aust. J. Chem., 1986, 39, 1643-1653.
Karuso et al., "The constituents of marine sponges. I. The isolation from Aplysilla sulphurea (Dendroceratida) of (1 R*, 1'S*, 1'R*,3R*)-1 -Acetoxy-4-ethyl-5-(1,3,3-trimethylcyclohexyl)-1,3- dihydroisobenzofuran-1'(4),3-carbolactone and the determination of its crystal structure," Aust. J. Chem., 1984, 37,1081-1093.
Keyzers et al., "Spongian diterpenoids from marine sponges," Nat. Prod. Reports, 2006, 23, 321-334.
Leiros et al., "Spongionella Secondary Metabolites Project Mitochondrial Function in Cortical Neurons against Oxidative Stress," Marine Drugs, 2014, 12: 700-718.
Römling et al., "Biofilm infections, their resilience to therapy and innovative treatment strategies," J. Int. Med., 2012, 272, 541-561.
Scali et al., "An update on chronic wounds and the role of biofilms," J. Cutan. Med. Surg., 2013,17, 371-376.
Sheldrick, "A short history of SHELX," Acta Cryst., 2008, A64, 112-122.
Sheldrick, "Phase annealing in SHELX-90: direct methods for larger structures," Acta Cryst., 1990, A46, 467-473.
Spek, "Structure validation in chemical crystallography," Acta Cryst., 2009, D65, 148-155.
Von Salm et al., "Darwinolide, a New Diterpene Scaffold That Inhibits Methicillin-Resistant *Staphylococcus aureus* Biofilm from the Antartic Sponge Dendrilla membranosa," Organic Letters, 2016, 18: 2596-2599.
Von Salm et al., "Shagenes A and B, New Tricyclic Sesquiterpenes Produced by an Undescribed Antarctic Octocoral," Org. Lett., 2014, 16, 2630-2633.
White et al., "Rearranged Diterpenes and Norditerpenes from Three Australian Goniobranchus Mollusks," Journal of Natural Products, 2015, 79: 477-483.

MRSA BIOFILM INHIBITION

CROSS-REFERENCE TO RELATED APPLICATION

This application claims priority to U.S. Provisional Patent Application No. 62/319,661, filed Apr. 7, 2016, which is incorporated herein by reference in its entirety.

STATEMENT OF GOVERNMENT SUPPORT

This invention was made with government support under Grant Numbers A 1103715, AI080626 and ANT0838773, PLR1341339 awarded by the National Institutes of Health and the National Science Foundation, respectively. The government has certain rights in the invention.

FIELD

Provided is an isolated darwinolide compound, compositions thereof, and methods of treating bacterial infection, such as those caused by methicillin-resistant *Staphylococcus aureus* (MRSA).

INTRODUCTION

Biofilms, such as those formed by *Staphylococcus aureus* and many other pathogenic bacteria during infection, are a collection of cells coated in an extracellular matrix comprised of polysaccharides, proteins and DNA. It is estimated that up to 80% of all infections are caused by bacterial biofilms, which are recalcitrant to therapeutic intervention. Indeed, at present there does not exist an effective option for controlling and eradicating biofilms during infection. Accordingly, there is a need to develop novel anti-biofilm agents to treat drug resistant bacterial infections. In particular, there is a need for an effective therapy for treating or preventing infections caused by bacteria that form biofilms.

SUMMARY

In one aspect, provided is an isolated darwinolide compound and a crystalline form thereof. The structure of the darwinolide compound is characterized herein by X-ray Diffraction Data, NMR, and mass spectra. Also provided are processes of isolating darwinolide and compositions comprising darwinolide.

In another aspect, provided are methods of inhibiting infection, including MRSA biofilm infection.

Other aspects of the invention will become apparent by consideration of the detailed description and accompanying drawings.

Figure 1:
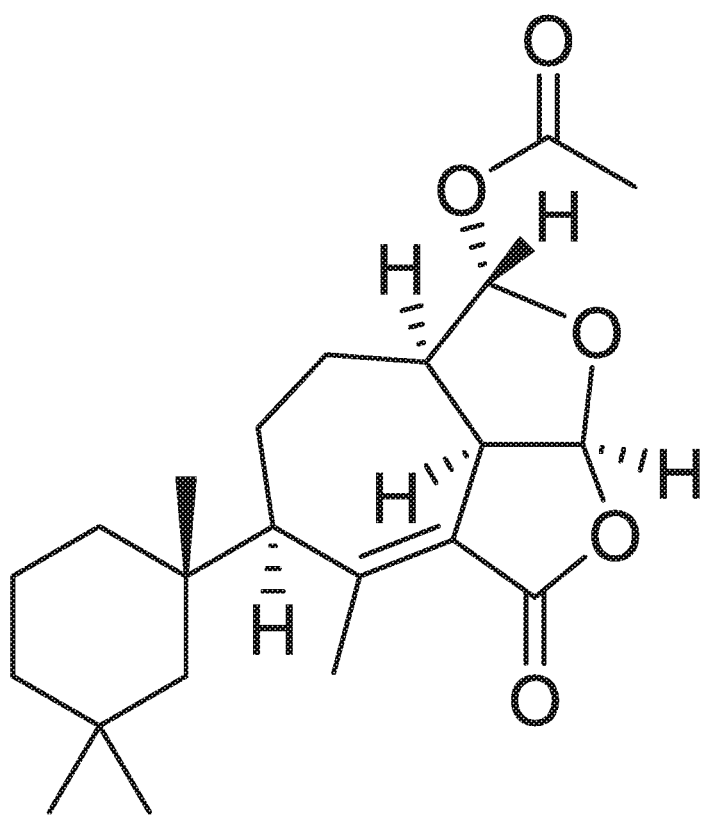
FIG. 1 depicts the structure of darwinolide.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

DETAILED DESCRIPTION

Disclosed herein is an isolated darwinolide compound, including its crystalline form, and compositions comprising the darwinolide compound. Also disclosed herein are processes of isolating darwinolide. The disclosed compound or compositions may be used to treat bacterial infections. The disclosed methods may be used to treat a subject with a bacterial infection. The bacteria that cause the infection may form a biofilm. The bacterial infection may be caused by methicillin-resistant *Staphylococcus aureus*. The methicillin-resistant *Staphylococcus aureus* may form a biofilm.

1. DEFINITIONS

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "administration" or "administering" as used herein may include the process in which the compounds or compositions as described herein, alone or in combination with other compounds or compositions, are delivered to a subject. The compound or compositions may be administered in various routes including, but not limited to, oral, parenteral (including intravenous, intra-arterial, and other appropriate parenteral routes), intrathecally, intramuscularly, subcutaneously, colonically, rectally, and nasally, transcutaneously, among others. The dosing of the agents, compounds, and compositions described herein to obtain a therapeutic or prophylactic effect may be determined by the circumstances of the subject, as known in the art. The dosing of a subject herein may be accomplished through individual or unit doses of the compounds or compositions herein or by a combined or prepackaged or pre-formulated dose of a compounds or compositions.

Administration may depend upon the amount of compound or composition administered, the number of doses, and duration of treatment. For example, multiple doses of the agent may be administered. The frequency of administration of the compound or composition may vary depending on any of a variety of factors, such as extent of anxiety-related behavior, and the like. The duration of administration of the compound or composition, e.g., the period of time over which the compound or composition is administered, may vary, depending on any of a variety of factors, including subject response, etc.

The amount of the compound or composition contacted (e.g., administered) may vary according to factors such as the degree of susceptibility of the individual, the age, sex, and weight of the individual, idiosyncratic responses of the individual, the dosimetry, and the like. Detectably effective amounts of the compounds or compositions of the present disclosure may also vary.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

As used herein, the term "IC$_{50}$" quantifies the ability of a compound or composition to inhibit a specific biological or biochemical function. The IC$_{50}$ may refer to the concentration of a compound or composition that kills 50% of bacterial cells. The IC$_{50}$ may refer to the concentration of a compound or composition that inhibits biofilm formation by 50%.

The use of "including," "comprising," or "having" and variations thereof herein is meant to encompass the items listed thereafter and equivalents thereof as well as additional items. Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

As used herein, the term "MIC" or "minimum inhibitory concentrations" means the minimum concentration of including, but not limited to, an antibiotic, drug, agent, chemical, compound, or composition, that prevents visible growth of bacteria.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and includes an excipient, diluent, carrier, and adjuvant that are acceptable for veterinary use and/or human pharmaceutical use. "A pharmaceutically acceptable excipient, diluent, carrier and/or adjuvant" as used herein includes one or more such excipients, diluents, carriers, and adjuvants.

As used herein, the term "subject," "patient," or "organism" includes humans and mammals (e.g., mice, rats, pigs, cats, dogs, and horses). Typical subjects to which an agent(s) of the present disclosure may be administered may include mammals, particularly primates, especially humans. For veterinary applications, suitable subjects may include, for example, livestock such as cattle, sheep, goats, cows, swine, and the like; poultry such as chickens, ducks, geese, turkeys, and the like; and domesticated animals particularly pets such as dogs and cats. For diagnostic or research applications, suitable subjects may include mammals, such as rodents (e.g., mice, rats, hamsters), rabbits, primates, and swine such as inbred pigs and the like. The subject may be immunocompromised. The subject may be immunosuppressed.

The "therapeutically effective amount" for purposes herein may be determined by such considerations as are known in the art. A therapeutically effective amount of a compound (such as darwinolide) may include the amount necessary to provide a therapeutically effective result in vivo. The amount of the compound or composition must be effective to achieve a response, including but not limited to a total prevention of (e.g., protection against) of a condition, improved survival rate or more rapid recovery, improvement or elimination of symptoms associated with the condition (such as drug resistant biofilm infection caused by MRSA), or other indicators as are selected as appropriate measures by those skilled in the art. As used herein, a suitable single dose size includes a dose that is capable of preventing or alleviating (reducing or eliminating) a symptom in a subject when administered one or more times over a suitable time period. The "therapeutically effective amount" of a compound or composition as described herein may depend on the route of administration, type of subject being treated, and the physical characteristics of the subject. These factors and their relationship to dose are well known to one of skill in the medicinal art, unless otherwise indicated.

As used herein, "treat", "treatment", "treating", and the like refer to acting upon a condition with an agent to affect the condition by improving or altering it. The condition includes, but is not limited to infection, such as those caused by bacteria. For example, the condition may include drug resistant bacterial biofilm infection caused by MRSA. The agent includes, but is not limited to, compounds or compositions capable of inhibiting or preventing infection, such as those caused by bacteria. For example, the agent may include the darwinolide compound or compositions described herein. The improvement or alteration may include an improvement in symptoms or an alteration in the physiologic pathways associated with the condition. The aforementioned terms cover one or more treatments of a condition in a subject (e.g., a mammal, typically a human or non-human animal of veterinary interest), and include: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reducing or eliminating the infection).

2. COMPOUND

Figure 2:
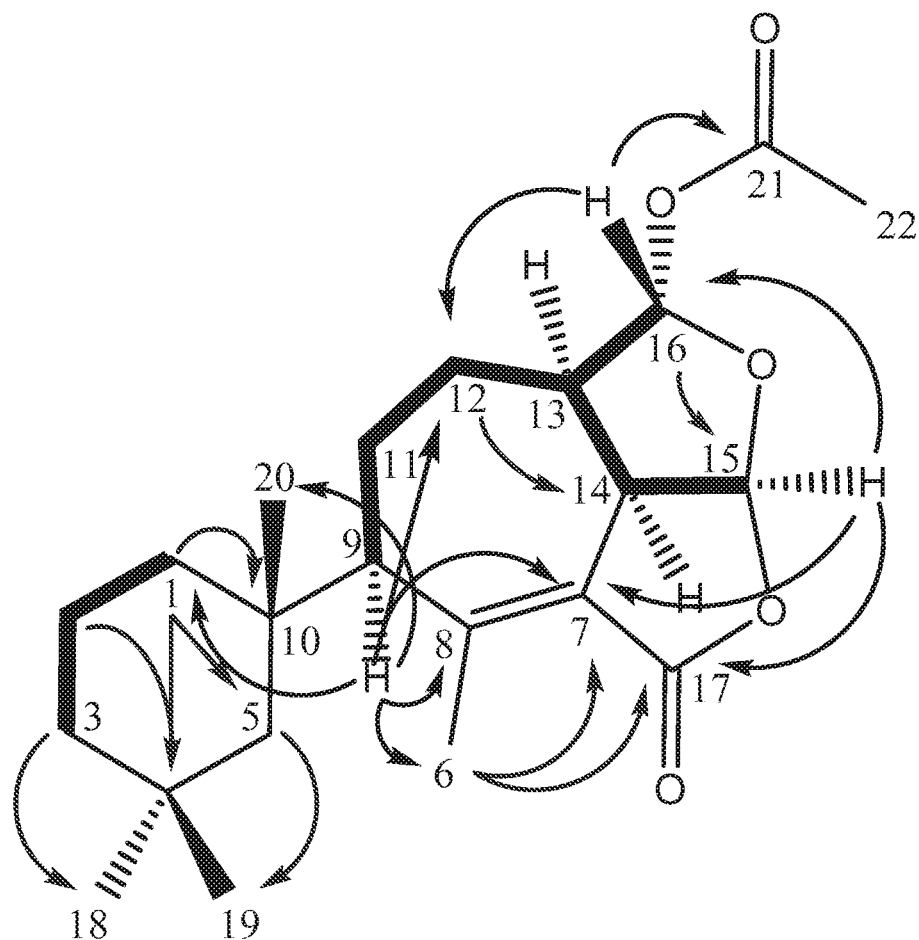
FIG. 2 depicts key COSY (bold) and HMBC (arrows) correlations observed for darwinolide.
Figure 3:
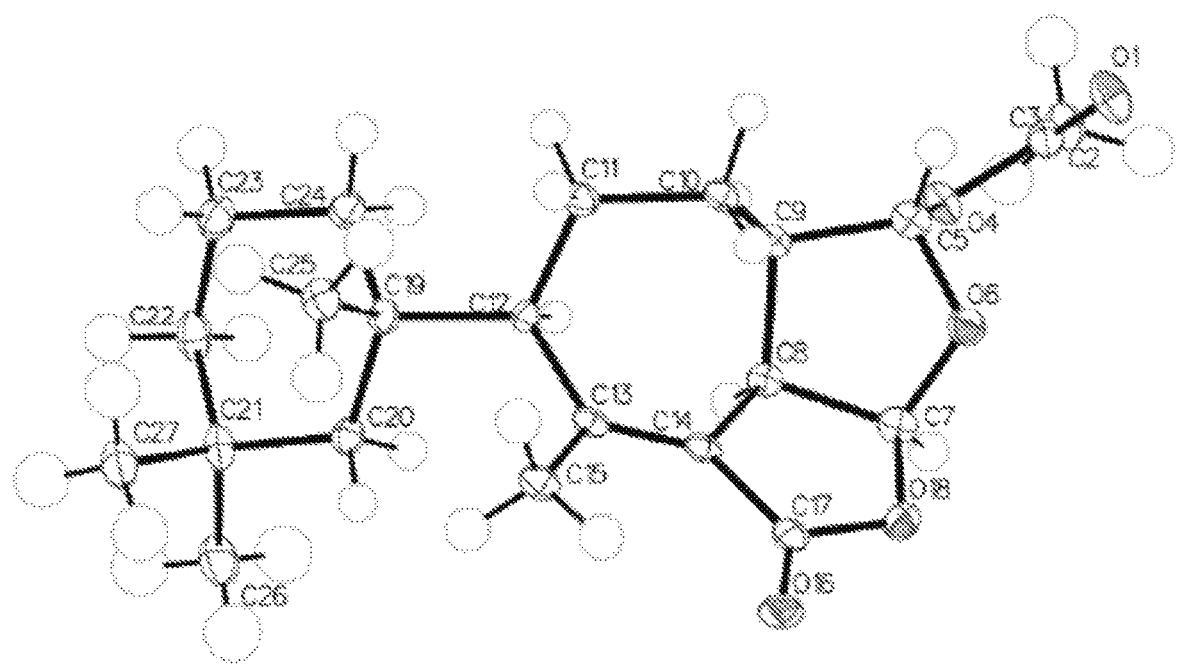
FIG. 3 depicts an asymmetric unit of darwinolide showing absolute stereostructure. Thermal ellipsoids have been drawn at 50% probability level.
Figure 4:
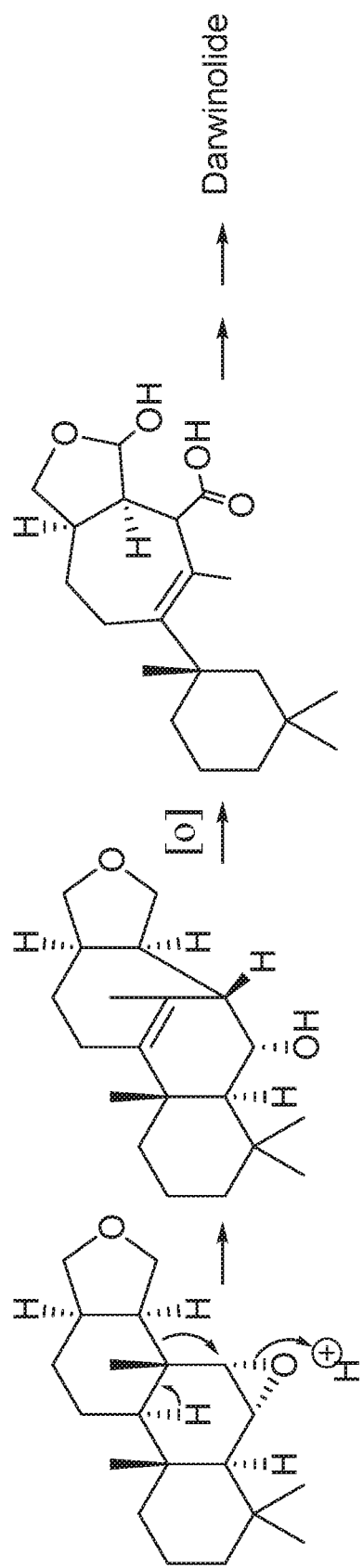
FIG. 4 depicts a proposed biosynthetic pathway for darwinolide.

In one aspect, disclosed is the darwinolide compound having the structure depicted in FIG. 1. The darwinolide compound may be isolated from the Antarctic Dendroceratid sponge *Dendrilla membranosa* as a new rearranged spongian diterpene. The darwinolide compound as described herein may be characterized by spectroscopic and crystallographic analyses. The results indicate that the darwinolide compound has a tricyclic ring system as core structure and six chiral centers (FIG. 2 and FIG. 3). The darwinolide compound may originate from a ring expansion of a spongian precursor and rearrangement (FIG. 4).

A crystalline form of the darwinolide compound is dissolved. The crystalline darwinolide compound may be obtained after isolation from the Antarctic Dendroceratid sponge *Dendrilla membranosa*. The crystalline darwinolide compound may be characterized by X-ray diffraction. For example, the crystalline darwinolide compound may demonstrate X-ray diffraction data: space group $P2_12_12_1$, a 7.6629(6) Å, b 9.5182(8) Å, c 27.012(2) Å. The crystal compound may have other characteristics as shown in Table 2 in Example 6.

Figure 5:
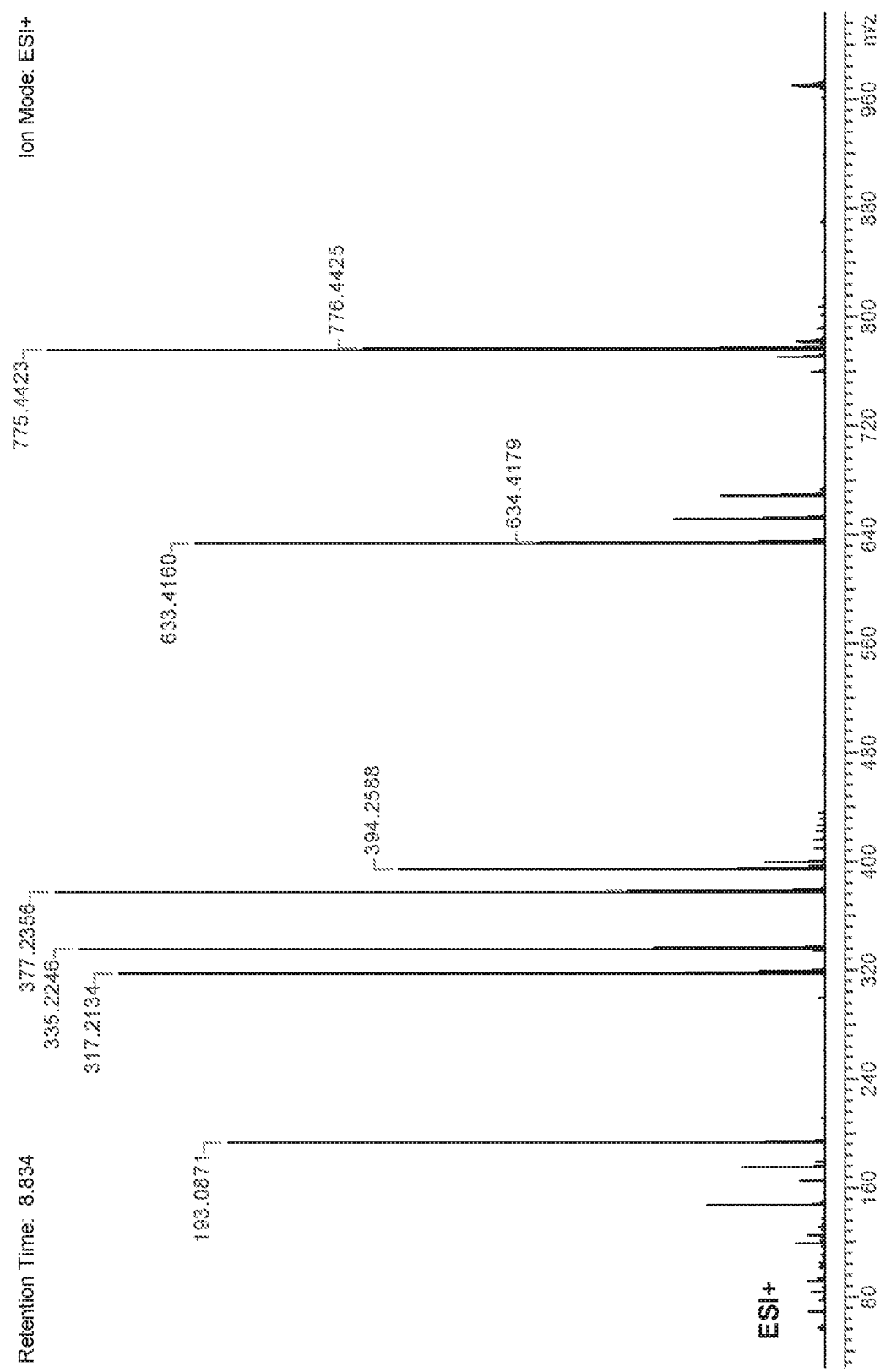
FIG. 5 is a HRESI+ mass spectrum of darwinolide.
Figure 6:
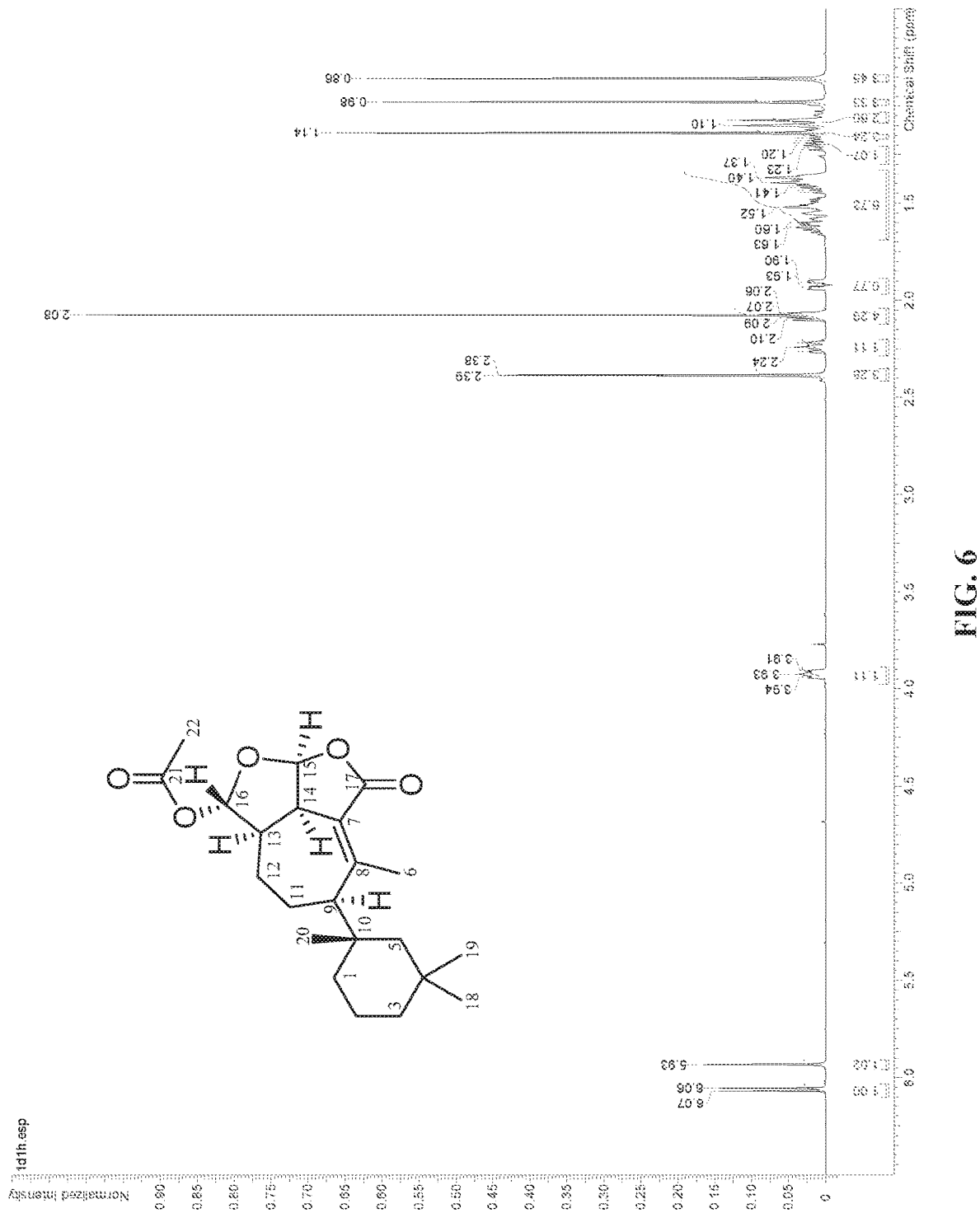
FIG. 6 is a $^1$H NMR spectrum of darwinolide in CDCl$_3$, 500 MHz.
Figure 7:
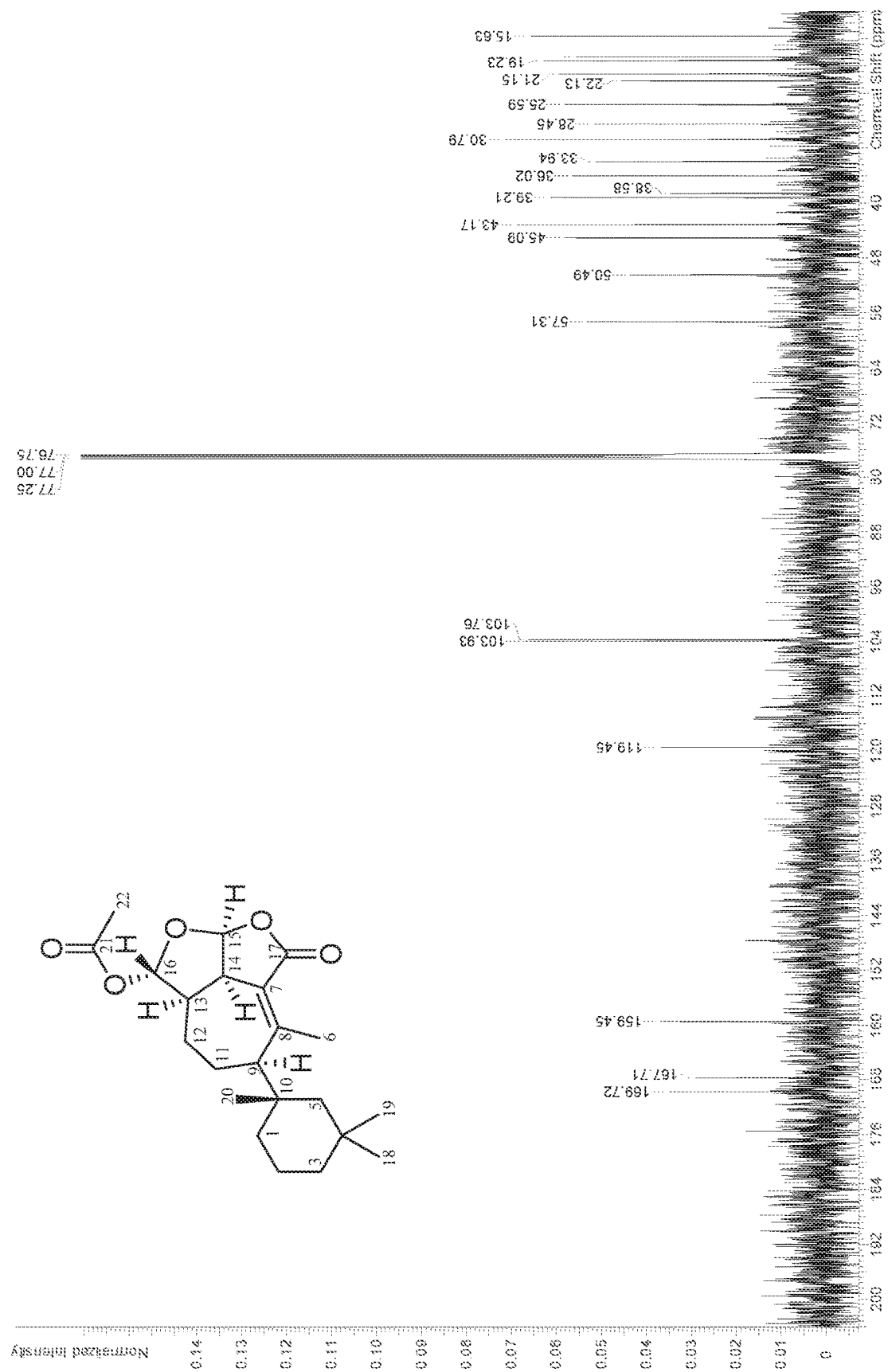
FIG. 7 is a $^{13}$C NMR spectrum of darwinolide in CDCl$_3$, 125 MHz.
Figure 8:
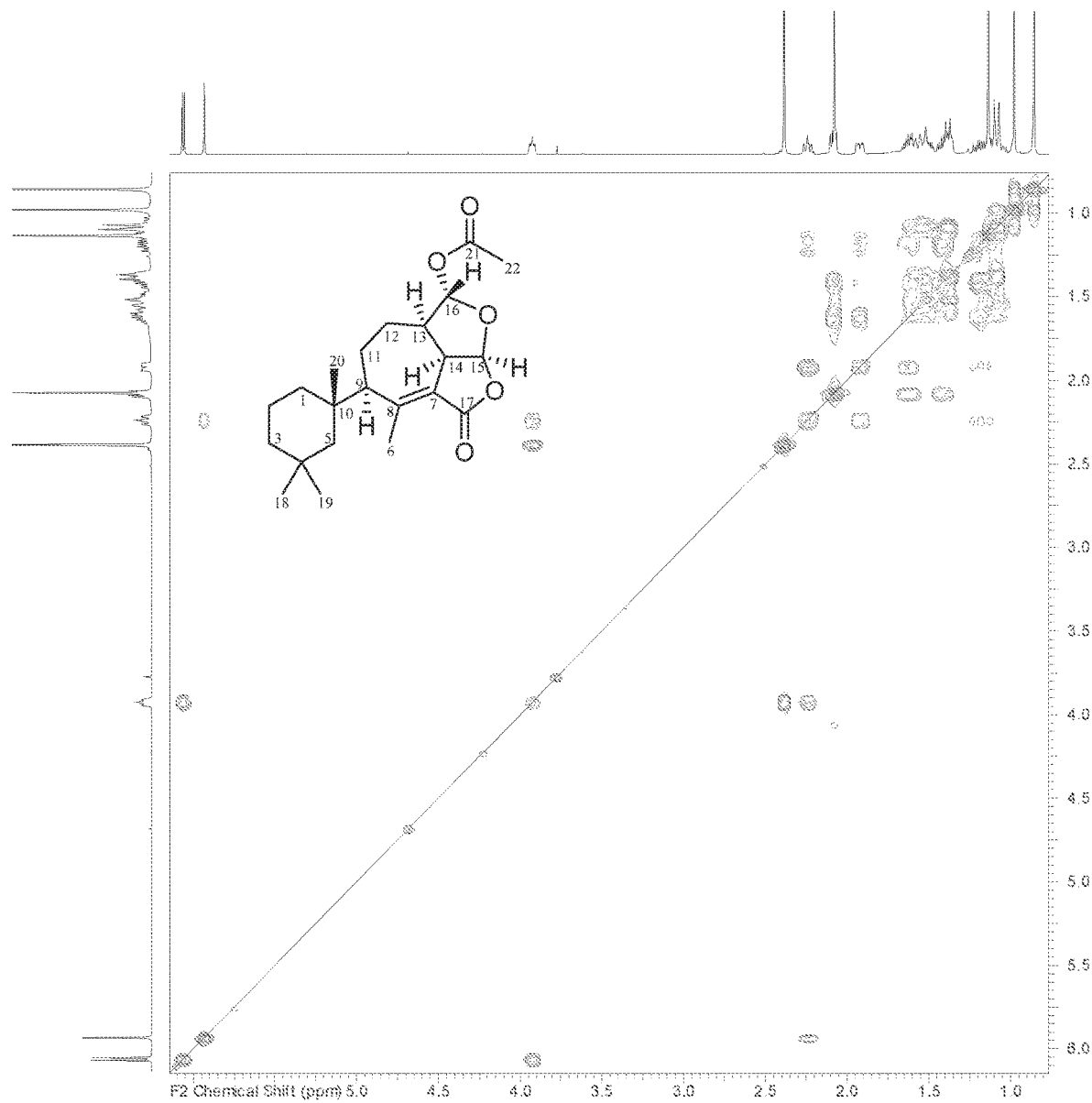
FIG. 8 is a gCOSY spectrum of darwinolide in CDCl$_3$, 500 MHz.
Figure 9A:
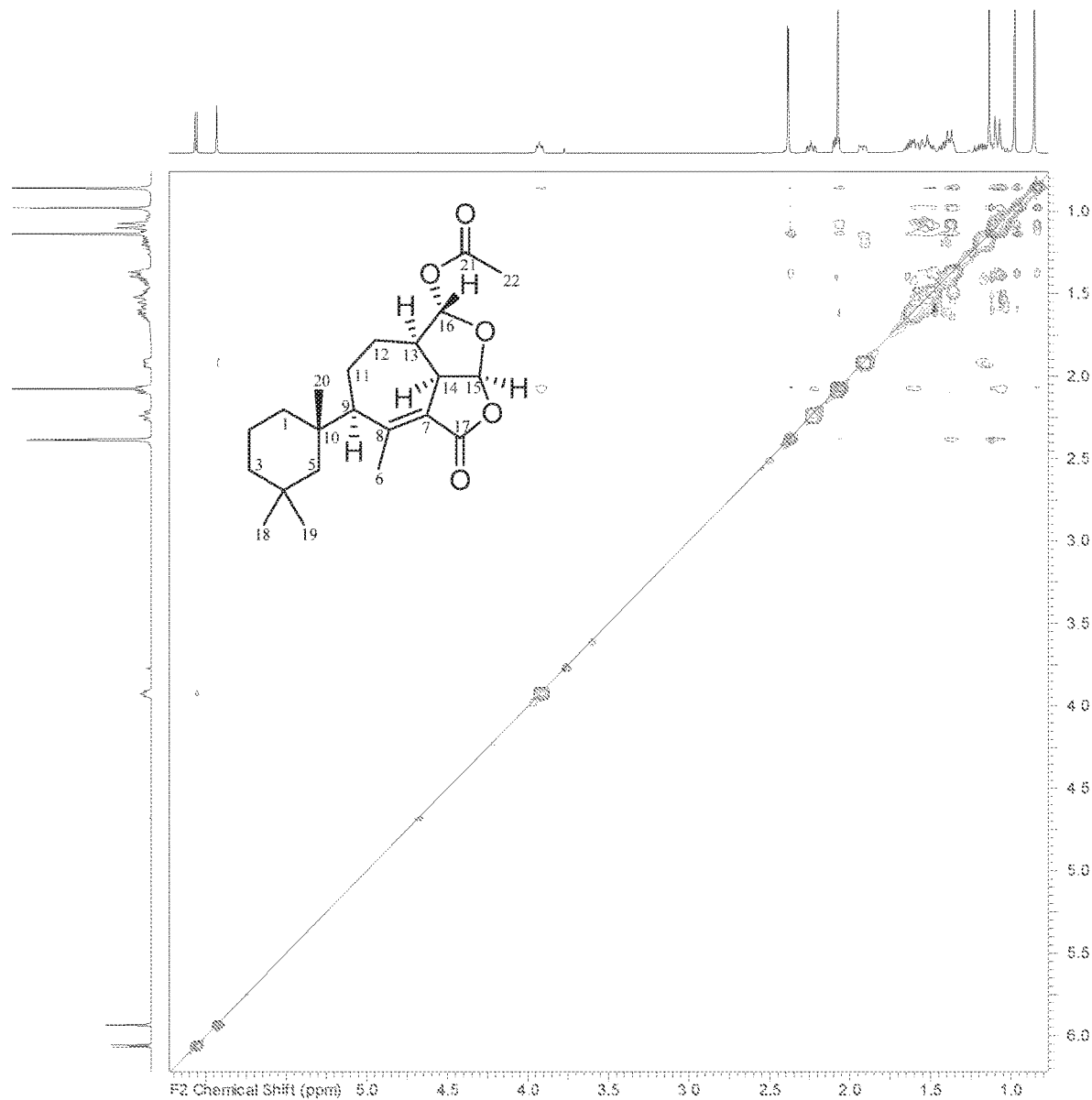
FIG. 9A is a ROESYAD spectrum of darwinolide in CDCl$_3$, 500 MHz.
Figure 9B:
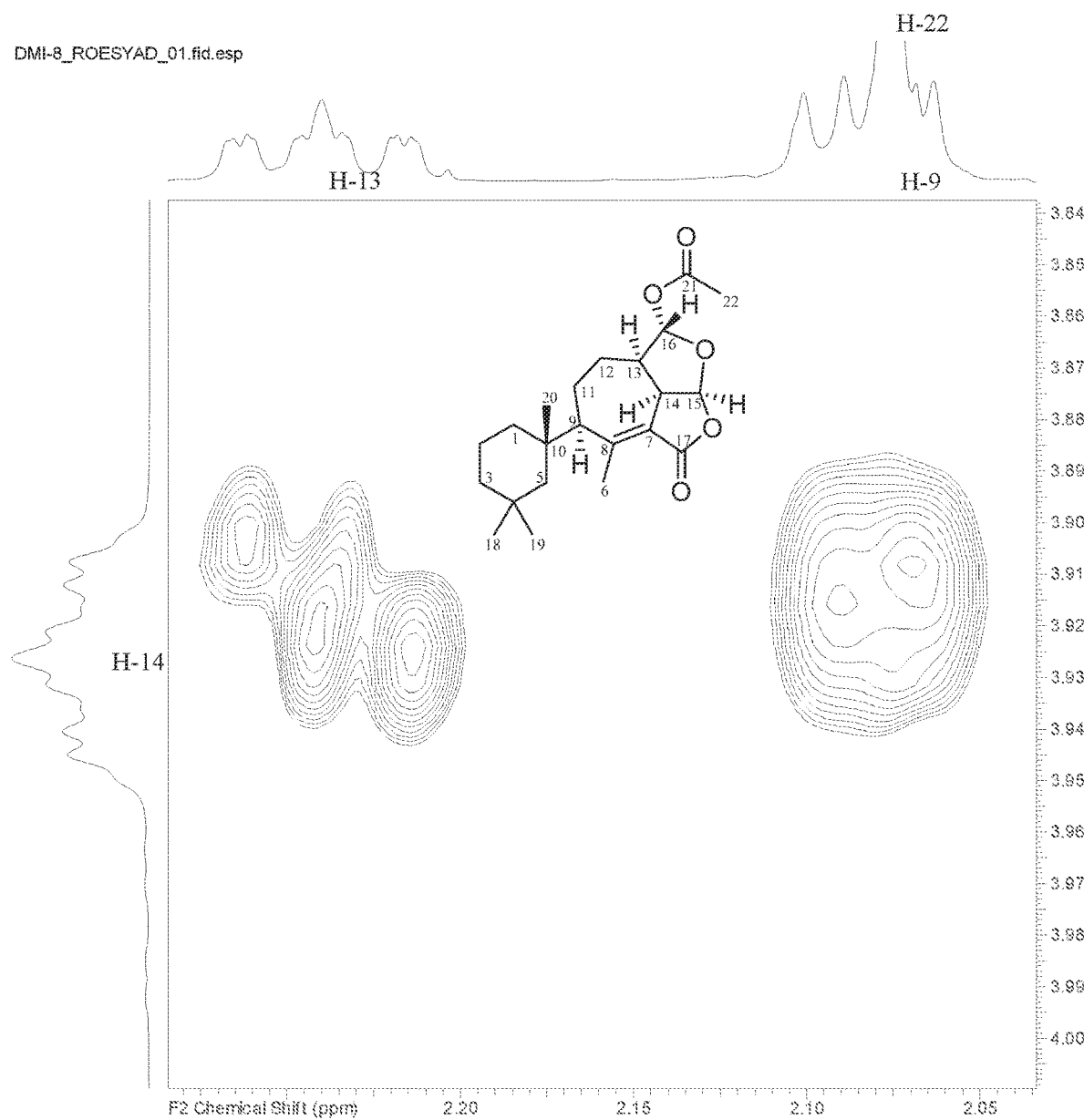
FIG. 9B shows an expansion of ROESYAD Spectrum of darwinolide (CDCl$_3$, 500 MHz) optimized to highlight important correlations of H-$_{14}$ (3.93 ppm).
Figure 10:
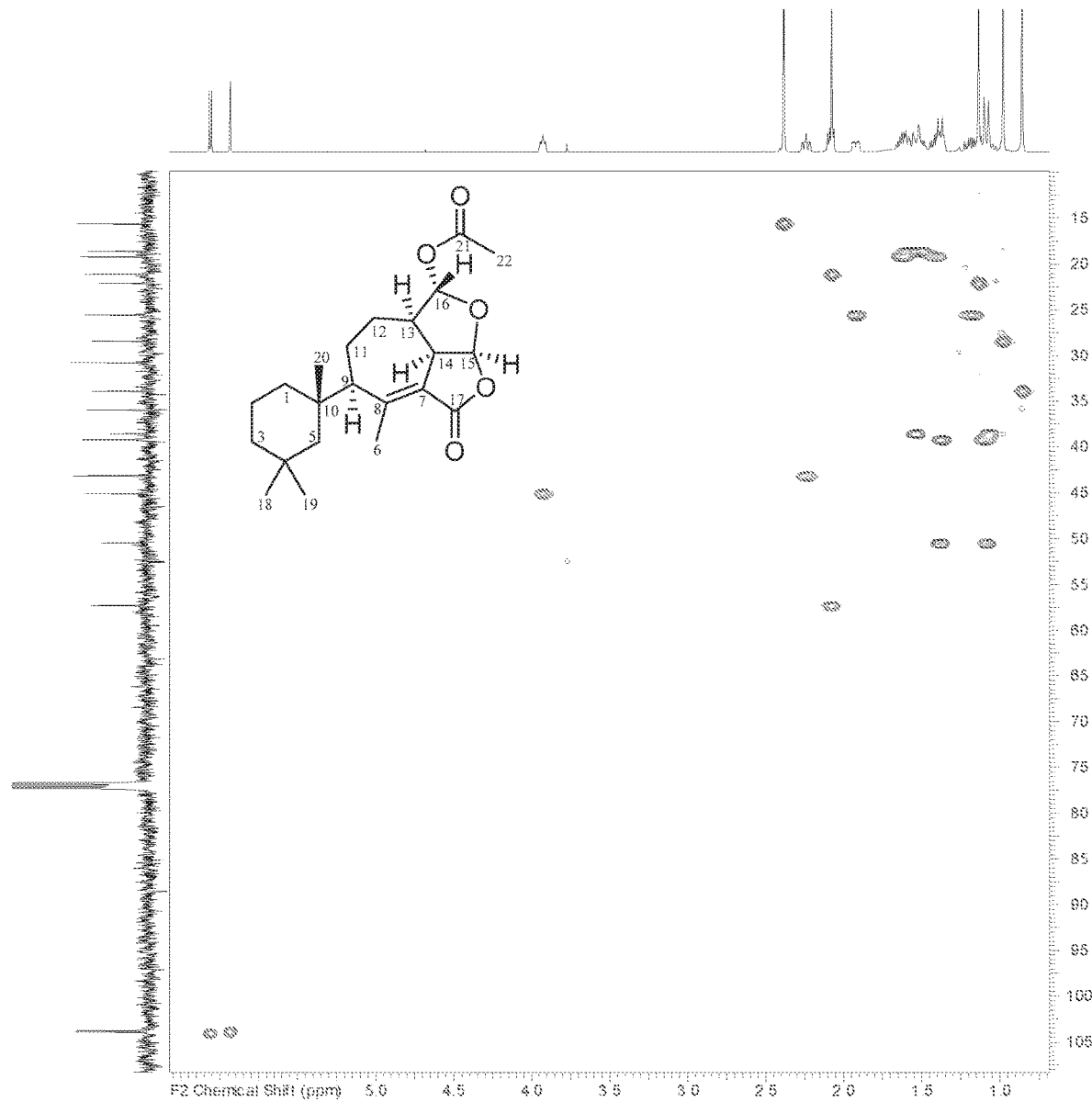
FIG. 10 is a gHSQCAD spectrum of darwinolide in CDCl$_3$, 500 MHz.
Figure 11:
FIG. 11 is a gHMBCAD spectrum of darwinolide in CDCl$_3$, 500 MHz.

The darwinolide compound may demonstrate characteristic peaks in mass spectrum. For example, the compound may show m/z peaks at 193.0871, 317.2134, 335.2246, 377.2356, 394.2588, 633.4160, and 775.4423 under positive ion mode ($M^+$) mass spectrum (FIG. 5.). The darwinolide compound may also demonstrate characteristic peaks in NMR spectra as shown, for example, by $^1$H NMR (FIG. 6), $^{13}$C NMR (FIG. 7), gCOSY (FIG. 8), ROESYAD (FIG. 9), gHSQCAD (FIG. 10), gHMBCAD (FIG. 11).

a. Isolation Process

In another aspect, the darwinolide compound disclosed herein may be isolated from a source. In some embodiments, the isolation method comprises the steps of:

(a) contacting a source of the darwinolide compound with an organic solvent to obtain a lipophilic extract;

(b) isolating the darwinolide compound from the lipophilic extract of step (a) using high-performance liquid chromatography (HPLC); and (c) optionally crystallizing the darwinolide compound obtained in step (b).

The organic solvent in step (a) may include polar and nonpolar solvents capable of dissolving the darwinolide compound in the source material. Upon contacting the source material, the solvent dissolves and extracts darwinolide into the organic phase to form a lipophilic extract. Suitable organic solvents may include, but are not limited to, methanol, ethanol, dichloromethane, chloroform, and combinations thereof. For example, suitable organic solvent for extraction may comprise halogenated solvents, such as dichloromethane.

The HPLC in step (b) may include eluting the darwinolide compound using a solvent system. In some embodiments, the solvent system for the elution comprises acetonitrile. In some embodiments, the HPLC may employ a gradient elution program, in which the solvent system may change from acetonitrile-water mixture to pure acetonitrile in a programmed manner. For example, the solvent system may include a gradient from 60% acetonitrile in water to 100% acetonitrile.

In some embodiments, the darwinolide compound may be isolated from the sponge *Dendrilla membranosa* from Antarctica.

3. PHARMACEUTICAL COMPOSITIONS

The darwinolide compound may be incorporated into pharmaceutical compositions suitable for administration to a subject (such as a human or non-human subject).

The pharmaceutical compositions may include a "therapeutically effective amount" or a "prophylactically effective amount" of the compound or composition. A "therapeutically effective amount" refers to an amount effective, at dosages and for periods of time necessary, to achieve the desired therapeutic result. A therapeutically effective amount of a compound or composition may be determined by a person skilled in the art and may vary according to factors such as the disease state, age, sex, and weight of the individual, and the ability of the compound or composition to elicit a desired response in the individual. A therapeutically effective amount is also one in which any toxic or detrimental effects of compounds or compositions of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound or composition of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the darwinolide compound and physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions typically are sterile and stable under the conditions of manufacture and storage.

The route by which the darwinolide compound is administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration may include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition may range from about 10 to about 90%, including from about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition may range from about 1% to about 20%, including from about 5% to about 10%

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition may range from about 10% to about 90%, including from about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may range from about 0.1% to about 10%.

Suitable colorants include a colorant such as an FD&C dye. When used, the amount of colorant in a systemic or topical composition may range from about 0.005% to about 0.1%.

Suitable flavors include menthol, peppermint, and fruit flavors. The amount of flavor(s), when used, in a systemic or topical composition may range from about 0.1% to about 1.0%.

Suitable sweeteners include aspartame and saccharin. The amount of sweetener(s) in a systemic or topical composition may range from about 0.001% to about 1%.

Suitable antioxidants include butylated hydroxyanisole ("BHA"), butylated hydroxytoluene ("BHT"), and vitamin E. The amount of antioxidant(s) in a systemic or topical composition may range from about 0.1% to about 5%.

Suitable preservatives include benzalkonium chloride, methyl paraben and sodium benzoate. The amount of preservative(s) in a systemic or topical composition may range from about 0.01% to about 5%.

Suitable glidants include silicon dioxide. The amount of glidant(s) in a systemic or topical composition range from about 1% to about 10%, including from about 1% to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition may range from 0% to about 100%.

Suitable suspending agents include AVICEL RC-591 (from FMC Corporation of Philadelphia, Pa.) and sodium alginate. The amount of suspending agent(s) in a systemic or topical composition may range from about 1% to about 10%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may range from about 0.1% to about 10%, including from about 0.1% to about 5%.

Although the amounts of components in the systemic compositions may vary depending on the type of systemic composition prepared, in general, systemic compositions include 0.01% to 50% of active compound and 50% to 99.99% of one or more carriers. Compositions for parenteral administration may include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount of darwinolide, usually at least about 0.1% by weight, including, for example, from about 1% to about 99%, from about 5% to about 95%, and from about 25% to about 75%. The oral dosage compositions may include from about 0.1% to about 99.9% by weight of carriers, including, for example, from about 1% to about 99%, from about 5% to about 95%, from about 10% to about 90%, from about 25% to about 75%, and from about 50% to about 75%.

Tablets can be compressed, tablet triturates, enteric-coated, sugar-coated, film-coated, or multiple-compressed. Tablets may include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) may include an active compound, and a carrier including one or more diluents disclosed above in a capsule comprising gelatin. Granules may comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings may include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions may include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the compounds to subjects include sublingual, buccal and nasal dosage forms. Such compositions may include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions may include an active compound (such as darwinolide) and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may range from about 5% to about 95%.

Suitable propellants include propane, butane, isobutane, dimethyl ether, carbon dioxide, nitrous oxide, and combinations thereof. The amount of propellant(s) in a topical composition may range from 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition may range from 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition may range from 0% to about 95%.

The amount of thickener(s) in a topical composition may range from 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may range from 0% to about 95%.

The amount of fragrance in a topical composition may range from 0% to about 0.5%, including, for example, from about 0.001% to about 0.1%.

Suitable pH adjusting additives include HCl or NaOH in amounts sufficient to adjust the pH of a topical pharmaceutical composition.

4. METHODS OF TREATMENT

The disclosed darwinolide compound and compositions may be used in methods for treatment of bacterial infections. The methods of treatment may comprise administering to a subject in need of such treatment a composition comprising a therapeutically effective amount of the darwinolide compound or compositions as disclosed herein. The methods of treatment may treat the bacterial infection by inducing bacterial cytotoxicity. The methods of treatment disclosed herein may treat the bacterial infection by preventing the formation of bacterial biofilms.

The compounds or compositions as disclosed herein may be useful for treating bacterial infections in a subject. Treatment of such infections may be effected by killing bacteria and/or preventing, slowing, or stopping the formation of bacterial biofilms, by administering a compound or compositions of this disclosure, either alone or in combination with another active agent as part of a therapeutic regimen to a subject in need thereof.

Thus, administering a therapeutically effective amount of the darwinolide compound and compositions disclosed herein may serve to eliminate bacterial infection in subjects. Specifically, the darwinolide compound and compositions disclosed herein may be useful for treating MRSA infections.

a. Bacterial Infections

Although bacteria may not be harmful, and in some cases may be beneficial, bacteria may also lead to infection. Bacterial infections can affect multiple organs and body systems including, but not limited to, skin, mucous membranes, blood, lungs, kidneys, urinary tract, eyes, heart, intestines, meninges, respiratory tract, genitals, stomach, bone, connective tissue, and tissue surrounding organs. Bacterial infections may affect more than one organ or body system. Bacterial infections may be systemic. Bacterial infections may be asymptomatic. Bacterial infections may cause a variety of symptoms including, but not limited to, fever, inflammation, wounds that do not heal, weeping wounds, skin rash, red bumps on the skin, abscesses, swollen lymph nodes, nausea, diarrhea, headaches, earaches, sore throat, fatigue, low blood pressure, hyperventilation, weak and rapid pulse, local or systemic pain, and muscle aches. Bacterial infections may cause death. Subjects with co-morbidities or a compromised immune system may be more susceptible to bacterial infections.

The diagnosis of a bacterial infection may include, but are not limited to, symptomatic diagnostics, microbial culture, microscopy, biochemical tests, PCR based diagnostics, and metagenomics sequencing. A microbial examination may include sample collection, microbial cultivation, identification, and test of antibiotic susceptibility. The diagnosis may include gram staining of the bacterial culture. The diagnosis may include a coagulase test of the bacterial culture. The diagnosis may include a catalase test of the bacterial culture. The diagnosis may include blood tests. The blood tests may include, but are not limited to, a full blood count, measurement of C-reactive protein, measurement of procalcitonin, and measurement of rapid plasma reagin. The diagnosis may include ELISA. The diagnosis may include PCR. A rapid latex agglutination test that detects the PBP2a protein may be conducted to identify MRSA. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The determination of bacteria growing on an agar plate or in a nutrient broth may determine the bacteria responsible for the subject's infection. Discs containing antibiotic compounds may be placed on the agar plates. The antibiotic compounds may kill the bacteria growing on the plate. The greater the zone of dead bacteria around the disc (zone of inhibition) may indicate a more effective antibiotic.

Samples for diagnosing a bacterial infection may be obtained from the subject in need of treatment. The sample for testing may be from the site of the infection. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and/or other body fluids. Multiple samples may be taken from the subject. Multiple samples may be taken around the site of a prosthesis or medical device.

Bacterial infections may be treated with the darwinolide compound and compositions disclosed herein. Bacterial infections that may be treated by the darwinolide compound and compositions disclosed herein include, but are not limited to, *Staphylococcus aureus*, methicillin-resistant *Staphylococcus aureus* (MRSA), *Enterococcus faecalis*, *Enterococcus faecium*, *Escherichia coli*, *Salmonella*, *Neisseria*, *Bacillus*, *Brucella*, *Nocardia*, *Listeria monocytogenes*, *Lactobacillus plantarum*, *Lactococcus lactis*, *Francisella*, *Legionella*, and *Yersinia pestis*, *Pseudomonas aeruginosa*, *Burkholderia cenocepacia*, and *Mycobacterium avium*. The bacterial infection to be treated may be resistant to one or many antibiotics. The bacterial infection to be treated may be caused by bacteria that form bacterial biofilms.

i) MRSA Infections

MRSA is any strain of *Staphylococcus aureus* that has developed multi-resistance to beta-lactam antibiotics, which include the penicillins (methicillin, dicloxacillin, nafcillin, oxacillin, etc.) and the cephalosporins. MRSA evolved from horizontal gene transfer of the mecA gene to at least five distinct *S. aureus* lineages. MRSA infections can quickly cause serious and life threatening internal infections including, but not limited to, sepsis, endocarditis, MRSA pneumonia bone infections, and infections of implants. MRSA may cause infections of the skin. The MRSA skin infections may lead to boils or abscesses. MRSA may cause systemic or internal infections. Some MRSA infections are untreatable with currently available antibiotics, usually resulting in severe, debilitating infection, or death. The MRSA infection may occur in subjects who have been hospitalized, which is known as health care-associated MRSA (HA-MRSA). The MRSA infection may be spread by skin-to-skin contact, which is known as community-associated MRSA (CA-MRSA). Cases of MRSA have increased in livestock animals. CC398, a variant of MRSA, has emerged in animals and is found in intensively reared production animals (e.g., pigs, cattle, and poultry), where it can be transmitted to humans as LA-MRSA (livestock-associated MRSA).

The strains of MRSA to be treated by the darwinolide compound and compositions disclosed herein may include, but are not limited to, CBD-635, ST250 MRSA-1, ST2470-MRSA-I, ST239-MRSA-III, ST5-MRSA-II, ST5-MRSA-IV, ST239-MRSA-III, EMRSA15, EMRSA16, MRSA252, ST5:USA100, EMRSA 1, ST8:USA300, ST1:USA400, ST8:USA500, ST59:USA1000, USA1100, USA600, USA800, USA300, ST30, ST93, ST80, ST59, CC22, CCB, CC425, and CC398.

ii) Bacterial Biofilms

A biofilm is known as a structured consortium attached on a living or inert surface formed by microbial cells sticking to each other and surrounded by an extracellular polymeric matrix that is produced by the microbes. The development of biofilm may include several stages. The stages may include attachment to a surface, formation of microcolonies, development of young biofilm, differentiation of structured mature biofilm, and dispersal of mature biofilm. Biofilm bacterial cells may be significantly more resistant to antibiotics and host immune defense than bacteria of the same species growing outside of a biofilm.

Bacterial biofilm formation is widely found in natural environments with water, and also in human diseases, especially in the subjects with indwelling devices for the purpose of medical treatments. It has been reported that the vast majority, if not all, of the medical devices or prostheses may result in biofilm infections. The medical devices or prostheses which may form biofilms include, but are not limited to, intravenous catheters, vascular prosthesis, cerebrospinal fluid shunts, prosthetic heart valves, urinary catheters, joint prostheses and orthopedic fixation devices, cardiac pacemakers, peritoneal dialysis catheters, intrauterine devices, biliary tract stents, dentures, breast implants, contact lenses, and in the dental area caries and periodontitis. Bacterial biofilm infections that are not associated with foreign bodies may also occur. Bacterial biofilm infections may include but are not limited to, chronic airway infections in subjects with cystic fibrosis (CF) or chronic obstructive pulmonary diseases, native valve endocarditis, chronic otitis media, chronic sinusitis, chronic wound infections, and diabetic wound infections. It has been estimated that most bacterial infections in human are correlated with biofilm and about 50% of the nosocomial infections are indwelling devices-associated.

Bacteria that may form biofilms include, but are not limited to, methicillin-resistant *Staphylococcus aureus*, *Staphylococcus aureus*, *Bacillus* spp, *Listeria monocytogenes*, *Lactobacillus plantarum*, *Lactococcus lactis*, *Escherichia coli*, and *Pseudomonas aeruginosa*.

The darwinolide compound and compositions described herein demonstrates modes of action toward eliminating bacterial infection, including preventing biofilm formation. The darwinolide compound or compositions thereof may be administered to a subject in need thereof to reduce, render bacteriostatic, eliminate, or otherwise inhibit infection, such as a MRSA biofilm infection. For example, the compound or composition may reduce the area of infection, improve recovery from infection, prevent worsening of infection, or even prevent occurrence of infection in the subject in need thereof.

b. Modes of Administration

Methods of treatment may include any number of modes of administering a disclosed compound or composition. Modes of administration may include tablets, pills, dragees, hard and soft gel capsules, granules, pellets, skin patches, skin creams, skin gels, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the compound or compositions disclosed herein may be admixed with adjuvants and excipients, such as gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the compound or compositions disclosed herein may also be dispersed in a microparticle, e.g. a nanoparticulate composition.

For parenteral administration, the compounds or compositions disclosed herein may be dissolved or suspended in a physiologically acceptable diluent, such as water, buffer, oils with or without solubilizers, surface-active agents, dispersants or emulsifiers. Suitable oils may include, for example, olive oil, peanut oil, cottonseed oil, soybean oil, castor oil and sesame oil. For parenteral administration, the compound or compositions disclosed herein may be administered in the form of an aqueous, lipid, oily or other kind of solution or suspension, or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

The darwinolide compound and compositions disclosed herein may be administered topically. A topical composition disclosed herein may be applied to the skin of a subject in need thereof. The area of skin selected for treatment may be the site of a bacterial infection. The area of skin selected for treatment may be skin surrounding the infection site. The area of skin selected for treatment may be the site of a bacterial infection and the skin surrounding the infection site. The infection of the skin may be caused by MRSA. A topical composition disclosed herein may be applied to a mucous membrane of a subject in need thereof. The mucous membrane selected for treatment may be the site of a bacterial infection. The area of the mucous membrane selected for treatment may be the mucous membrane surrounding the bacterial infection. The mucous membrane selected for treatment may be the site of a bacterial infection and the mucous membrane surrounding the site of the infection. The infection of the mucous membrane may be caused by MRSA.

The topical administration may be with a patch containing the compound and compositions disclosed herein. The topical administration may be with a dissolvable patch containing the compound and compositions disclosed herein. The topical administration may be with a cream containing the compound and compositions disclosed herein. The topical administration may be with foam containing the compound and compositions disclosed herein. The topical administration may be with lotion containing the compound and compositions disclosed herein. The topical administration may be with an ointment containing the compound and compositions disclosed herein. The topical administration may be with gel containing the compound and compositions disclosed herein. The topical administration may have fewer side effects than systemic administration of antibiotics.

In some embodiments, a topical composition comprising a therapeutically effective amount of the darwinolide compound and compositions disclosed herein may be applied to the infected skin and/or mucous membrane of a subject to reduce or eliminate the infection, and/or improve healing of the wounded skin and/or mucous membrane. In particular embodiments, a topical composition comprising a therapeutically effective amount of the darwinolide compound and compositions disclosed herein may be applied to an area of the skin and/or mucous membrane infected by MRSA, including infections caused by MRSA biofilm. In these embodiments, the darwinolide compound and compositions disclosed herein may be administered alone or in combination of one or more other active agents to reduce infection and/or promote skin and/or mucous membrane healing.

c. Combination Therapies

Additional therapeutic agent(s) may be administered simultaneously or sequentially with the darwinolide compound and compositions. Sequential administration includes administration before or after the disclosed compound and compositions. An additional therapeutic agent may be administered before the disclosed compound and compositions. An additional therapeutic agent may be administered after the disclosed compound and compositions. An additional therapeutic agent may be administered at the same time as the disclosed compound and compositions. In some embodiments, the additional therapeutic agent or agents may be administered in the same composition as the disclosed compounds. In other embodiments, there may be an interval of time between administration of the additional therapeutic agent and the disclosed compound or compositions. In some embodiments, administration of an additional therapeutic agent with a disclosed compound or compositions may allow lower doses of the other therapeutic agents and/or administration at less frequent intervals. When used in combination with one or more other active ingredients, the compound or compositions of the present invention and the other active ingredients may be used in lower doses than when each is used singly. Accordingly, the pharmaceutical compositions of the present invention include those that contain one or more other active ingredients, in addition to a compound of the present disclosure.

For the treatment of bacterial infection, the darwinolide compound and compositions may be combined with a variety of antibiotics. The antibiotics include, but are not limited to, vancomycin, linezolid, teicoplanin, ceftaorline, clindamycin, mupirocin, trimethoprim-sulfamethoxazole, tetracyclines, daptomycin, sulfa drugs, ceftobiprole, ceftaroline, dalbavancin, telavancin, torezolid, iclaprim, nemonoxacin, platensimycin, and oxadiazoles.

The darwinolide compound and compositions may be combined with agents that inhibit bacterial biofilm formation. The agents that inhibit bacterial biofilm formation include, but are not limited to, imidazole derivatives, indole derivatives, emodin, flavonoids, ginger extracts, *Hypericum perforatum*, 7-epiclusianone, isolimonic acid, tannic acid, chelerythrine, carvacrol, bgugaine, resveratrol, garlic extracts, natural halogenated furanones, brominated alkylidene lactams, and AHLs-based inhibitors.

The darwinolide compound and compositions may be combined with lysine-conjugated aliphatic norspermidine analogues. The darwinolide compound and compositions may be combined with phage therapy. In the case of infection involving a medical device or prosthesis, the darwinolide compound and compositions may be administered in combination with the removal of the medical device or prosthesis. A new, sterile medical device or prosthesis may be implanted in the subject.

The darwinolide compound and compositions may be combined with agents to modify potential side effects from antibacterial agents. Agents that may mediate or treat side effects include, but are not limited to, probiotics, anti-diarrheal agents, anti-emetic agents, and analgesics.

The subject may also be undergoing a variety of treatments for co-morbidities.

d. Evaluation of Treatment

The efficacy of the methods of treatment with the darwinolide compound and compositions disclosed herein may be measured. The status of the bacterial infection may be monitored. The efficacy of the methods of treatment disclosed herein may be evaluated by the same or similar methods as used for diagnosis of the bacterial infection.

Evaluating the efficacy of the methods of treatment with the darwinolide compound and compositions disclosed herein or monitoring the bacterial infection may include, but are not limited to, symptomatic diagnostics, microbial culture, microscopy, biochemical tests, PCR based tests, and metagenomics sequencing. A microbial examination may include sample collection, microbial cultivation, identification, and test of antibiotic susceptibility. The evaluation or monitoring may include gram staining of the bacterial culture. The evaluation or monitoring may include a coagulase test of the bacterial culture. The evaluation or monitoring may include a catalase test of the bacterial culture. The evaluation or monitoring may include blood tests. The blood tests may include, but are not limited to, a full blood count, measurement of C-reactive protein, measurement of procalcitonin, and measurement of rapid plasma reagin. The evaluation or monitoring may include ELISA. The evaluation or monitoring may include PCR. A rapid latex agglutination test that detects the PBP2a protein may be conducted to identify MRSA. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The presence, decreased presence, or lack of bacteria growing on an agar plate or in a nutrient broth may determine that the bacterial infection is improving or has been eradicated.

Samples for determining the efficacy of the methods of treatment with the darwinolide compound and compositions disclosed herein or monitoring the bacterial infection, may be obtained from the subject. The sample for testing may be from the site of the infection, or the site where the infection was previously present. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and/or other body fluids. Multiple samples may be taken from the subject. Multiple samples may be taken around the site of a prosthesis or medical device.

The evaluation of the efficacy of methods of treatment with the darwinolide compound and compositions disclosed herein or monitoring of the bacterial infection may indicate that the subject requires continued treatment with the darwinolide compound and compositions disclosed herein. The evaluation of the efficacy of methods of treatment with darwinolide compound and compositions disclosed herein or monitoring of the bacterial infection may indicate the eradication of the bacterial infection in the subject. The eradication of the bacterial infection may indicate that the subject no longer requires treatment with the darwinolide compound and compositions disclosed herein.

5. KITS

The darwinolide compound or compositions may be included in kits comprising the compound, a systemic or topical composition, or both; and information, instructions, or both that use of the kit will provide treatment for medical conditions in mammals (particularly humans). The kit may include an additional pharmaceutical composition for use in combination therapy. The kit may include buffers, reagents, or other components to facilitate the mode of administration. The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

6. EXAMPLES

Example 1. Chemical Extraction, Isolation, and Characterization

Extraction. In the course of acquiring biodiversity to support an antibiotic screening program, the current inventors obtained the sponge Dendrilla membranosa from the vicinity of Palmer Station, Antarctica. The dichloromethane extract of the freeze-dried sponge was subjected to reversed-phase solid-phase extraction eluted with acetonitrile. The extract underwent HPLC purification to yield four major natural products, including three previously reported spongian diterpenes: aplysulphurin, tetrahydroaplysulphurin, and membranolide (Karuso et al., Aust. J. Chem. 1984, 37, 1081-1093; Karuso et al., Aust. J. Chem. 1986, 39, 1643-1653; and Molinski et al., J. Org. Chem. 1989, 54, 3902-3907). The fourth product was identified as darwinolide, a new rearranged spongian diterpene having a structure shown in FIG. 1. The darwinolide compound was isolated herein as white crystals; $[\alpha]^{23}D+53$ (c 1.0, CHCl3); UV-Vis (CH$_3$CN) $\lambda_{max}$ (log ε): 240 (4.73), 233 (4.73), 215 (4.77) nm; IR (thin film): 3049, 2921, 1756, 1636, 1372, 1234 cm$^{-1}$; HRESIMS m/z 377.2356 [M+H]$^+$ (calculated for 377.2328 C$_{22}$H$_{33}$O$_5$); 317.2134 [M−HOAc+H]$^+$ (calc'd 317.2117); 335.2246 [M−OAc+H$_2$O]$^+$ (calc'd 335.2222); 394.2588 [M+H$_2$O]$^+$ (calc'd 394.2355); 633.4160 [2(M−HOAc)+H]$^+$ (calc'd 633.4155); 775.4423 [2M+Na]$^+$ (calc'd 775.4397). The darwinolide skeleton is the newest of over a dozen structural motifs distinguishing the broad chemodiversity found in the Darwinellidae family of sponges.

The chemical formula of darwinolide, C$_{22}$H$_{32}$O$_5$, was determined from the HRESIMS (m/z 377.2356 [M+H]$^+$, calculated 377.2328), corroborating the $^{13}$C NMR spectrum, which displayed correlations in the HSQC spectrum indicative of six quaternary, five methine, six methylene and five methyl carbons (Table 1). The methyl group signals observed in the $^1$H NMR spectrum were similar to those of the other spongian diterpenes found in the extract. A gem-dimethyl group (δ 0.86, 0.98) was evident, as was a singlet angular-type methyl group at δ 1.14, and vinyl and acetoxy methyl groups at δ 2.39 and 2.08, respectively. The low-field shift of the vinyl methyl group, taken with its small (2.3 Hz) coupling, is reminiscent of tetrahydroaplysulphurin-3. Other notable $^1$H NMR signals include downfield singlet and doublet signals of the acetal methines (δ 5.93, 6.07).

TABLE 1

NMR Data for Darwinolide (CDCl$_3$)

| Position | $\delta_C$, type[a] | $\delta_H$ (J in Hz)[b] | HMBC | ROESY |
|---|---|---|---|---|
| 1a | 38.6, | 1.08, m | 2, 3, 4, 9, 18, 19, 20 | |
| b | | 1.54, m | 2, 3, 4, 5, 10, 20 | |
| 2 a | 18.7, | 1.50, m | 1, 4, 10 | |
| b | | 1.59, m | 4 | |
| 3a | 39.2, | 1.11, m | 2, 4, 18, 19 | |
| b | | 1.37, m | 4, 10, 18, 19 | |
| 4 | 30.8, C | | | |
| 5 a | 50.5, | 1.08, d (14.1) | 3, 4, 9, 18, 19, 20 | |
| b | | 1.38, d (14.1) | 1, 2, 3, 4, 11, 18, 19, 20 | |
| 6 | 15.6, | 2.39, d (2.3) | 7, 8, 9, 13, 17 | 20 |
| 7 | 119.5, C | | | |
| 8 | 159.5, C | | | |
| 9 | 57.3, CH | 2.08, m | 1, 5, 6, 7, 8, 10, 11, 12, 20 | 14 |
| 10 | 36.0, C | | | |
| 11 a | 19.2, | 1.42, m | 8, 9, 10, 12, 13, 16 | |
| b | | 1.64, m | 8, 9, 12, 13 | |
| 12 a | 25.6, | 1.92, m | 9, 13, 14, 16 | |
| b | | 1.19, m | 13, 14, 16 | |
| 13 | 43.2, CH | 2.24, m | 12, 16 | |
| 14 | 45.1, CH | 3.93, tt (7.0, | 7 | 9, 13, |
| 15 | 103.9, CH | 6.07, d (7.0) | 7, 14, 17 | 14 |
| 16 | 103.8, CH | 5.93, s | 12, 13, 14, 15, 21 | 12a |
| 17 | 167.7, C | | | |
| 18 | 33.9, | 0.86, s | 2, 3, 4, 5, 10, 19 | 19 |
| 19 | 28.5, | 0.98, s | 3, 4, 5, 10, 18 | 18 |
| 20 | 22.1, | 1.14, s | 1, 5, 9, 10 | 6 |
| 21 | 169.7, C | | | |
| 22 | 21.2, | 2.08, s | 16, 21 | |

[a]Recorded at 125 MHz; recorded at 500 MHz

The COSY spectrum showed coupling among most of the protons comprising the core tricyclic ring system (FIG. 2). Coupling of H$_2$-1/H$_2$-2 and H$_2$-2/H$_2$-3 observed in the COSY spectrum, in addition to HMBC correlations of H$_b$-1 (δ 1.54) to C-3, C-4, C-5, C-10, and C-20, and H$_3$-20 (δ 1.14) to C-1, C-5, C-9 and C-10, helped to establish the tri-methyl cyclohexane ring found among gracilin- and aplysulphurin-type seco-spongian metabolites. The protons of the gem-dimethyl group on that substructure, H$_3$-18 and H$_3$-19, correlated in the HMBC to C-3, C-4 and C-5. A proton at δ 2.08 displayed HMBC correlations spanning the tricyclic core and the tri-methylcyclohexyl groups, including C-1, C-5, C-6, C-7, C-8, C-10, C-11, C-12, and C-20, securing its assignment as H-9. Completion of the carbon skeleton could be accomplished by observation of HMBC correlations of H-14 (δ 3.93) to C-7, C-8, C-13 and C-15. An acetate substituent was located at C-16 based on HMBC correlations between H-16 (δ 5.93) and carbonyl C-21, and the furan and furanone ring systems were required by HMBC correlation of H-15 (δ 6.08) to acetal carbon C-16 and lactone carbon C-17.

The relative stereochemistry of the six chiral centers could be assigned with ROESY (Table 1), which demonstrated H-9, H-13, H-14 and H-15 occupied the same face of the tricyclic core, as did Ha-12 and H-16. These observations were confirmed by X-ray analysis (FIG. 3), which also established the absolute configuration of darwinolide.

Without being limited by any theory, it is hypothesized that darwinolide may be derived biosynthetically from the same gracilane pathway as other known aplysulphurides (Keyzers et al., Nat. Prod. Reports 2006, 23, 321-334), but with a rearrangement not previously observed (FIG. 4). Rather than a C-8 to C-7 methyl shift of C-17 resulting from elimination of H-9, as observed in other spongian rearrangements, a carbon shift from C-14 to C-7 ring expansion forms the new seven-membered carbocyclic ring.

Spongian diterpenes are well known as bioactive natural products. Darwinolide was screened for activity against a clinical strain of a highly resistant Staphylococcus aureus (MRSA). A broth dilution assay determined the MIC for darwinolide as 132.9 μM. The remaining colony was subjected to a cell recovery experiment overnight after washout of darwinolide. This study revealed that only 1.6% of the treated bacterium was able to recover and grow, therefore indicating darwinolide was cytotoxic, rather than cytostatic, toward *S. aureus*. A biofilm was established in vitro with the same MRSA strain, and the experiment revealed an $IC_{50}$ value of 33.2 μM against the biofilm. Cytotoxicity against a J774 macrophage cell line found darwinolide lacks mammalian cytotoxicity ($IC_{50}$=73.4 μM). Based on the 4-fold selectivity of darwinolide for MRSA biofilms over planktonic cells, and its low mammalian cytotoxicity, darwinolide presents a highly suitable scaffold for the development of urgently needed, novel anti-biofilm-specific antibiotics.

Isolation. All solvents were obtained from FISHER SCIENTIFIC CO. and were HPLC grade (>99% purity) unless otherwise stated. All HPLC analysis was performed on a SHIMADZU LC20-AT system equipped with a photodiode array detector (M20A) using semi-preparative [PHENOMENEX LUNA C18 (250×10 mm, 5 μm)] or analytical [PHENOMENEX LUNA SILICA (250×4.6 mm, 5 μm)] conditions. Analytical LCMS was performed on a PHENOMENEX KINETEX C18 column (50×2.1 mm, 2.6 μm) with an AGILENT 6540 LC/QToF-MS with electrospray ionization detection. Optical rotations were measured on a RUDOLPH Research Analytical AUTOPOL IV digital polarimeter. Other spectroscopic data was collected on an AGILENT CARY 630 FTIR or CARY 60 UV-Vis spectrometer. All NMR spectra were acquired in $CDCl_3$ with residual solvent referenced as an internal standard (7.26 ppm). All $^1H$ NMR spectra were recorded on a VARIAN 500 MHz direct-drive instrument equipped with cold-probe detection and $^{13}C$ NMR spectra were recorded at 125 MHz.

Example 2. Collection of *Dendrilla membranosa*

Sponge samples were collected from various sites around Palmer Station, Antarctica in the austral summer of 2011. The collection sites chosen were Norsel Point (64° 45.674'S, 64° 05.467'W), Bonaparte Point (64° 46.748'S, 64° 02.542'W), Gamage Point (64° 46.345'S 64° 02.915'W), and Laggard Island (64° 48.568'S, 64 00.984'W) at depths between 5-35 m below sea level. Samples were frozen and transported back to the University of South Florida at −70° C. where tissues were lyophilized and stored at −80° C. until further processing.

Example 3. Extraction and Isolation of Natural Products 25.7 g of freeze-dried *D. membranosa* was extracted with dichloromethane (ACS grade) in triplicate, combined, and concentrated in vacuo. The lipophilic extract (994 mg) was absorbed onto WATERS SEP-PAK® C18 cartridges and eluted with acetonitrile. The dried eluate (205 mg) was separated by isocratic semi-preparative HPLC using 60% acetonitrile in water for 35 min and ramping up to 100% acetonitrile after 50 min to afford (in retention time order) membranolide A (8.7 mg), aplysulphurin (10.2 mg), tetrahydroaplysulphurin (1.5 mg), and darwinolide (2.0 mg).

Example 4. Cytotoxicity Assay

The J774.A-1 cell line was used for cytotoxicity screening via a colorometric method employing a tetrazolium derivative [3-(4,5-dimethylthiazol-2-yl)-5-(3-carboxymethoxyphenyl)-2-(4-sulfophenyl)-2H-tetrazolium] (MTS) 72 h assay using 50000 amastigotes per well, and an electron-coupling reagent, and penazine methosulphate (PMS) were used in the assay. $IC_{50}$ values were calculated from sigmoidal inhibition curves using SigmaPlot 11.0 software (von Salm et al., J. Org. Lett. 2014, 16, 2630-2633).

Example 5. Assay Against Methicillin-Resistant *Staphylococcus aureus*

A clinical, multi-drug resistant strain of MRSA (CBD-635) was used in these studies for minimum inhibitory concentration (MIC) determination and assessment of anti-biofilm properties, all as described previously (Fleeman et al., J. Med. Chem. 2015, 58, 3340-3355).

Example 6. X-ray Diffraction Data for Darwinolide

The X-ray diffraction data for darwinolide were measured on BRUKER SMART APEX2 and for remaining crystals, on BRUKER D8 VENTURE PHOTON 100 CMOS system equipped with a Cu $K_\alpha$ INCOATEC ImuS micro-focus source (λ=1.54178 Å). Indexing was performed using APEX2[1] (Difference Vectors method, Bruker APEX2 (V2013.6-2), 2014, Bruker AXS Inc., Madison, Wis., USA). Data integration and reduction were performed using SAINTPLUS 6.01 (Bruker SAINT (V8.32A), Data Reduction Software. 2013, Bruker AXS Inc., Madison, Wis., USA). Absorption correction was performed by multi-scan method implemented in SADABS (Sheldrick, G. M. SADABS, Program for Empirical Absorption (Correction), 1996, University of Gottingen, Germany). Space group was determined using XPREP implemented in APEX3 [1]. Structure was solved using SHELXS-97 (direct methods) and refined using SHELXL-2015 (full-matrix least-squares on $F^2$) through OLEX2 interface program (as described in Sheldrick, G. M. SHELXL-97, Program for Crystal Structure Refinement, 1997, University of Gottingen, Germany; Sheldrick, G. M. Acta Cryst. 1990, A46, 467-473; Sheldrick, G. M. Acta Cryst. 2008, A64, 112-122; and Dolomanov et al., J. Appl. Cryst. 2009, 42, 339-341). All non-hydrogen atoms were refined anisotropically. Hydrogen atoms of —CH, —$CH_2$ and —$CH_3$ groups were placed in geometrically calculated positions and were included in the refinement process using riding model with isotropic thermal parameters: Uiso(H)=1.2[1.5]Ueq(—CH,—$CH_2$,[—$CH_3$]). Table 3 shows the results of Bijvoet-Pair Analysis and Bayesian Statistics validating the absolute configuration assignment (Spek, A. L. Acta Cryst. 2009, D65, 148-155; Hooft et al., J. Appl. Cryst. 2008, 41, 96-103). Value of "P2" is a probability that the current model is correct assuming two possibilities only—one of the two possible enantiomers present. Crystal data and refinement conditions are shown in Table 2. The asymmetric unit of darwinolide is shown in FIG. 3.

TABLE 2

Crystal data and structure refinement

| | |
|---|---|
| Identification code | JF_DMI8_0m |
| Empirical formula | $C_{22}H_{32}O_5$ |
| Formula weight | 376.47 |
| Temperature/K | 100 |
| Crystal system | orthorhombic |
| Space group | $P2_12_12_1$ |
| a/Å | 7.6629(6) |
| b/Å | 9.5182(8) |
| c/Å | 27.012(2) |
| α/° | 90 |
| β/° | 90 |

TABLE 2-continued

Crystal data and structure refinement

| | |
|---|---|
| $\gamma/°$ | 90 |
| Volume/Å$^3$ | 1970.2(3) |
| Z | 4 |
| $\rho_{calc}$g/cm$^3$ | 1.269 |
| $\mu$/mm$^{-1}$ | 0.714 |
| F(000) | 816.0 |
| Crystal size/mm$^3$ | 0.21 × 0.03 × 0.02 |
| Radiation | CuKα ($\lambda$ = 1.54178) |
| 2Θ range for data collection/° | 6.544 to 136.638 |
| Index ranges | $-9 \leq h \leq 9$, $-11 \leq k \leq 11$, $-32 \leq l \leq 32$ |
| Reflections collected | 14341 |
| Independent reflections | 3600 [$R_{int}$ = 0.0724, $R_{sigma}$ = 0.0530] |
| Data/restraints/parameters | 3600/0/249 |
| Goodness-of-fit on F$^2$ | 1.049 |
| Final R indexes [I >= 2σ (I)] | $R_1$ = 0.0425, $wR_2$ = 0.0889 |
| Final R indexes [all data] | $R_1$ = 0.0560, $wR_2$ = 0.0951 |
| Largest diff. peak/hole/e Å$^{-3}$ | 0.21/−0.23 |
| Flack parameter | 0.03(16) |

TABLE 3

Bijvoet-Pair analysis, Bayesian statistics and asymmetric unit of darwinolide

| | |
|---|---|
| Space Group | P212121 |
| Wavelength | 1.54178 |
| Flack x | 0.03(16) |
| Parsons z | 0.07(16) |
| Bijvoet Pairs | 1501 |
| Coverage | 99 |
| DiffCalcMax. | 23.54 |
| Outlier Crit | 47.08 |
| Scatter Plot | |
| Sigma Crit | 0.25 |
| Select Pairs | 15 |
| Number Plus | 12 |
| Number Minus | 3 |
| Slope | 1.574 |
| Student-T Prob. Plot | |
| Sample Size. | 1491 |
| Corr. Coeff. | 0.999 |
| Intercept | 0.042 |
| Slope | 0.892 |
| Bayesian Statistics | |
| Student_T Nu | 100 |
| Select Pairs | 1501 |
| Theta_Min | 7.60 |
| Theta_Max | 68.32 |
| P2(true) | 1.000 |
| P3(true) | 0.944 |
| P3(rac-twin) | 0.056 |
| P3(false) | 0.5E-06 |
| G | 0.8188 |
| G(su) | 0.3353 |
| Hooft y | 0.09(17) |

FIGS. 5-11 depict full NMR and mass spectra and details of the crystal analysis, as described herein.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense. It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1. A method of treating infection in a in a subject in need thereof, the method comprising administering to the subject an effective amount of darwinolide compound having a formula of

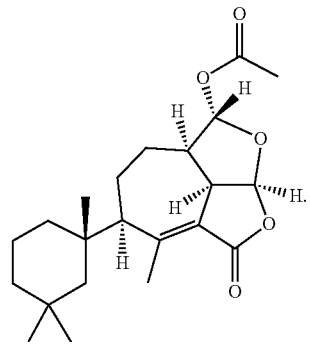

Clause 2. The method of clause 1, wherein the infection is a bacterial infection.

Clause 3. The method of clause 2, wherein the bacterial infection is caused by MRSA.

Clause 4. The method of clause 2, wherein the bacterial infection is caused by bacteria that form a bacterial biofilm.

Clause 5. The method of clause 4, wherein the bacterial biofilm is a MRSA bacterial biofilm.

Clause 6. The method of clause 2, wherein the bacterial infection is resistant to treatment with one or more antibiotics.

Clause 7. The method of clause 4, wherein the darwinolide compound inhibits bacterial biofilm formation.

Clause 8. The method of clause 1, wherein the darwinolide compound is combined with a pharmaceutically acceptable carrier.

Clause 9. The method of clause 8, wherein the darwinolide compound and pharmaceutically acceptable carrier is administered orally, intravenously, transdermally, or topically.

Clause 10. The method of clause 9, wherein the darwinolide compound and pharmaceutically acceptable carrier is administered topically.

Clause 11. The method of clause 10, wherein the darwinolide compound and pharmaceutically acceptable carrier is administered topically to an area of the skin and/or mucous membrane infected by MRSA.

Clause 12. A crystalline form of darwinolide compound having a formula of

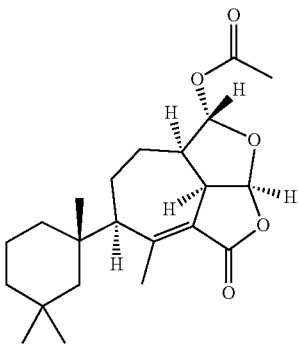

wherein the crystalline compound demonstrates X-ray diffraction data: space group $P2_12_12_1$, a 7.6629(6) Å, b 9.5182(8) Å, c 27.012(2) Å.

Clause 13. A process of isolating darwinolide compound, comprising the steps of:
(a) contacting a source of the darwinolide compound with an organic solvent to obtain a lipophilic extract;
(b) isolating the darwinolide compound from the lipophilic extract of step (a) using high-performance liquid chromatography; and
(c) optionally crystallizing the darwinolide compound obtained in step (b),
wherein the darwinolide compound has a formula of

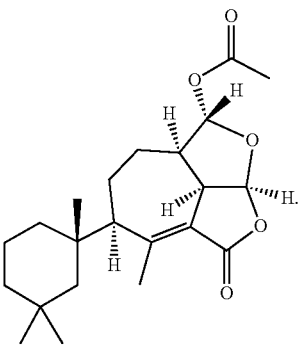

Clause 14. The process of clause 13, wherein the organic solvent in step (a) is selected from the group consisting of methanol, ethanol, dichloromethane, chloroform, and combinations thereof.

Clause 15. The process of clause 13, wherein the organic solvent in step (a) is dichloromethane.

Clause 16. The process of clause 13, wherein the high-performance liquid chromatography of step (b) comprises eluting the darwinolide compound using a solvent system comprising acetonitrile.

Clause 17. The process of clause 16, wherein the solvent system comprises a gradient from 60% acetonitrile in water to 100% acetonitrile.

Clause 18. The process of clause 13, wherein the source of the darwinolide compound is *Dendrilla membranosa*.

Clause 19. A pharmaceutical composition comprising at least one pharmaceutically acceptable carrier and an effective amount of darwinolide compound having a formula of

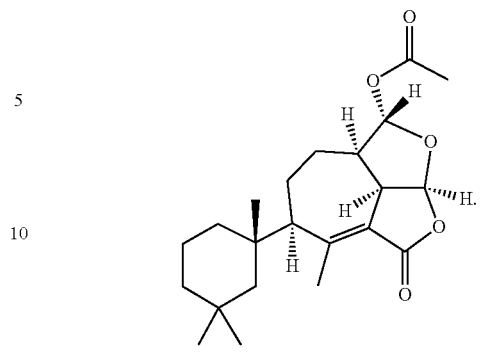

It is also to be understood that the following claims are intended to cover all of the generic and specific features of the invention herein described, and all statements of the scope of the invention that, as a matter of language, might be said to fall therebetween.

What is claimed is:

1. A method of treating infection in a subject in need thereof, the method comprising administering to the subject an effective amount of darwinolide compound having a formula of

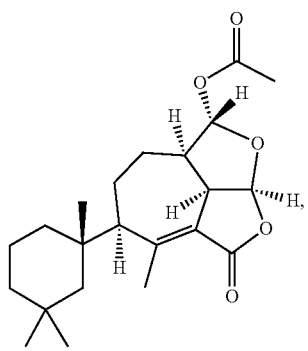

wherein the infection is a bacterial infection.

2. The method of claim 1, wherein the bacterial infection is caused by MRSA.

3. The method of claim 1, wherein the bacterial infection is caused by bacteria that form a bacterial biofilm.

4. The method of claim 3, wherein the bacterial biofilm is a MRSA bacterial biofilm.

5. The method of claim 1, wherein the bacterial infection is resistant to treatment with one or more antibiotics.

6. The method of claim 3, wherein the darwinolide compound inhibits bacterial biofilm formation.

7. The method of claim 1, wherein the darwinolide compound is combined with a pharmaceutically acceptable carrier.

8. The method of claim 7, wherein the darwinolide compound and pharmaceutically acceptable carrier is administered orally, intravenously, trans-dermally, or topically.

9. The method of claim 8, wherein the darwinolide compound and pharmaceutically acceptable carrier is administered topically.

10. The method of claim 9, wherein the darwinolide compound and pharmaceutically acceptable carrier is administered topically to an area of the skin and/or mucous membrane infected by MRSA.

11. A crystalline form of darwinolide compound having a formula of

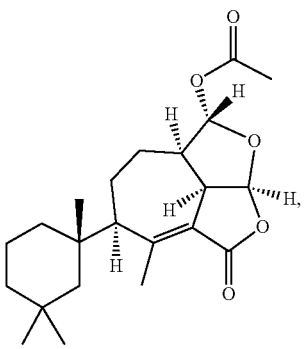

wherein the crystalline compound demonstrates X-ray diffraction data: space group $P2_12_12_1$, a 7.6629(6) A, b 9.5182(8) A, c 27.012(2) A.

12. A process of isolating darwinolide compound, comprising the steps of:
   (a) contacting a source of the darwinolide compound with an organic solvent to obtain a lipophilic extract;
   (b) isolating the darwinolide compound from the lipophilic extract of step (a) using high-performance liquid chromatography; and
   (c) optionally crystallizing the darwinolide compound obtained in step (b), wherein the darwinolide compound has a formula of 0

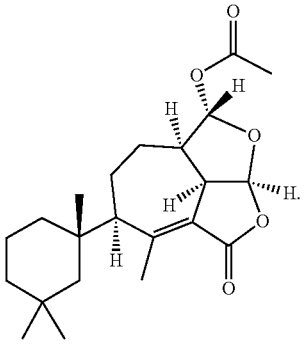

13. The process of claim 12, wherein the organic solvent in step (a) is selected from the group consisting of methanol, ethanol, dichloromethane, chloroform, and combinations thereof.

14. The process of claim 12, wherein the organic solvent in step (a) is dichloromethane.

15. The process of claim 12, wherein the high-performance liquid chromatography of step (b) comprises eluting the darwinolide compound using a solvent system comprising acetonitrile.

16. The process of claim 15, wherein the solvent system comprises a gradient from 60% acetonitrile in water to 100% acetonitrile.

17. The process of claim 12, wherein the source of the darwinolide compound is *Dendrilla membranosa*.

18. A pharmaceutical composition comprising at least one pharmaceutically acceptable carrier and an effective amount of darwinolide compound having a formula of

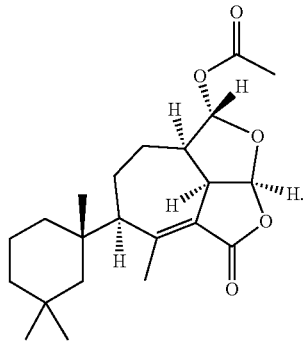

* * * * *